(12) United States Patent
Artsyukhovich et al.

(10) Patent No.: US 8,591,492 B2
(45) Date of Patent: Nov. 26, 2013

(54) IRRIGATION SOURCE IDENTIFICATION SYSTEM

(75) Inventors: Alexander N. Artsyukhovich, Irvine, CA (US); Raphael Gordon, Ladera Ranch, CA (US); Michael D. Morgan, Costa Mesa, CA (US); Gary P. Sorensen, Laguna Niguel, CA (US); Daniel J. Wilson, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/456,294

(22) Filed: Apr. 26, 2012

(65) Prior Publication Data

US 2013/0289494 A1 Oct. 31, 2013

(51) Int. Cl.
  *A61J 1/00*   (2006.01)
  *A61J 1/18*   (2006.01)
  *A61B 19/00*  (2006.01)

(52) U.S. Cl.
  USPC .......................................... 604/404; 604/408

(58) Field of Classification Search
  USPC .................................................. 604/403–416
  See application file for complete search history.

(56) References Cited

U.S. PATENT DOCUMENTS

| | | | | |
|---|---|---|---|---|
| 4,614,437 | A * | 9/1986 | Buehler | 366/130 |
| 2010/0168711 | A1* | 7/2010 | Bazargan et al. | 604/404 |
| 2011/0264069 | A1* | 10/2011 | Bochenko | 604/404 |
| 2012/0330684 | A1* | 12/2012 | Jacobs et al. | 705/3 |

* cited by examiner

*Primary Examiner* — Philip R Wiest
*Assistant Examiner* — Benjamin Klein
(74) *Attorney, Agent, or Firm* — Kenneth D. Bassinger

(57) ABSTRACT

An irrigation source identification system includes an irrigation source, an imaging device, and a processor. The irrigation source includes a container for holding a quantity of irrigation fluid and a port fluidly coupled to the container. The port has an outlet end and a neck. The neck has a plurality of protrusions selected from a grouping of protrusions. The plurality of protrusions provides a unique identifier for the container. An imaging device images the neck and the plurality of protrusions of the irrigation source, and the processor determines which identifier is associated with the image.

16 Claims, 4 Drawing Sheets

IRRIGATION SOURCE IDENTIFICATION SYSTEM

BACKGROUND OF THE INVENTION

The present invention relates to phacoemulsification surgery and more particularly to a system for identifying the type of irrigation source used during surgery.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece, an attached hollow cutting needle surrounded by an irrigation sleeve, and an electronic control console. The hand piece assembly is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece assembly.

The operative part in a typical hand piece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the hand piece by flexible mountings. The hand piece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigation sleeve.

During the phacoemulsification procedure, the tip of the cutting needle and the end of the irrigation sleeve are inserted into the anterior capsule of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a waste reservoir.

Throughout the procedure, irrigating fluid is introduced into the eye, passing between the irrigation sleeve and the cutting needle and exiting into the eye at the tip of the irrigation sleeve and/or from one or more ports, or openings, in the irrigation sleeve near its end. The irrigating fluid protects the eye tissues from the heat generated by the vibrating of the ultrasonic cutting needle. Furthermore, the irrigating fluid suspends the fragments of the emulsified lens for aspiration from the eye.

Irrigation fluid is typically held in a bottle or bag much as IV fluids are. The bottle or bag has an end in which a spike is inserted to connect the fluid source to flexible tubing for use during surgery. In some cases, different types, sources, or amounts of irrigation fluid may be used during the surgical procedure. For example, one irrigation fluid source may contain a certain amount of fluid while another source contains a different amount of fluid. The chemical make-up of the fluids may be different. Further, the type of bottle or bag holding the fluid may also be different or have unique characteristics. It would be desirable to have an automatic way of detecting the differences among irrigation fluid sources.

SUMMARY OF THE INVENTION

In one embodiment consistent with the principles of the present invention, the present invention is an irrigation source comprising a container for holding a quantity of irrigation fluid and a port fluidly coupled to the container. The port has an outlet end and a neck. The neck has a plurality of protrusions selected from a grouping of protrusions. The plurality of protrusions provides a unique identifier for the container.

In another embodiment of the present invention, the present invention is an irrigation source identification system comprising an irrigation source, an imaging device, and a processor. The irrigation source includes a container for holding a quantity of irrigation fluid and a port fluidly coupled to the container. The port has an outlet end and a neck. The neck has a plurality of protrusions selected from a grouping of protrusions. The plurality of protrusions provides a unique identifier for the container. An imaging device is located adjacent to the neck of the irrigation source. The processor is coupled to the imaging device. The imaging device images the neck and the plurality of protrusions of the irrigation source and the processor determines which identifier is associated with the image.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
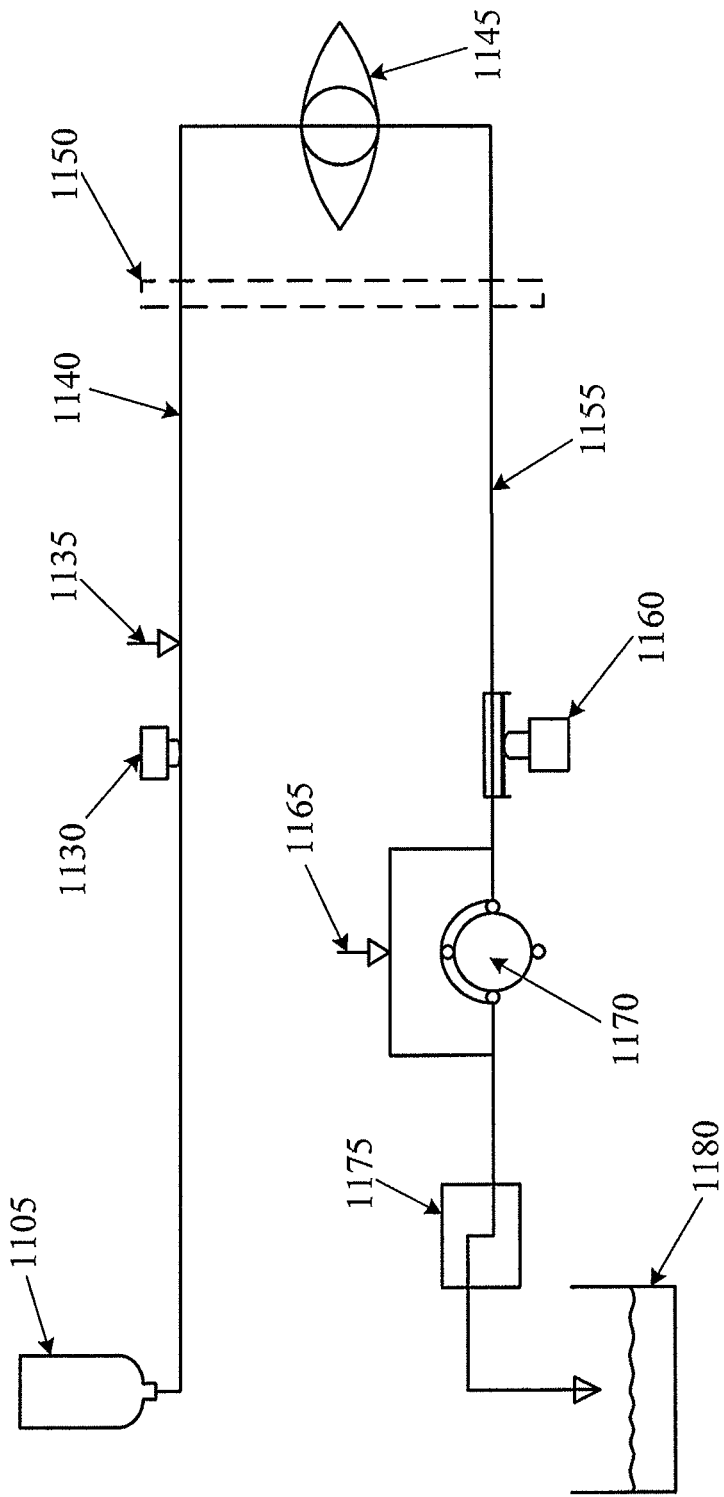
FIG. 1 is a diagram of the components in the fluid path of a phacoemulsification system.

FIG. 1 is a diagram of the components in the fluid path of a phacoemulsification system. FIG. 1 depicts the fluid path through the eye 1145 during cataract surgery. The components include an irrigation fluid source 1105, an irrigation pressure sensor 1130, an irrigation valve 1135, an irrigation line 1140, a hand piece 1150, an aspiration line 1155, an aspiration pressure sensor 1160, a vent valve 1165, a pump 1170, a reservoir 1175 and a drain bag 1180. The irrigation line 1140 provides irrigation fluid to the eye 1145 during cataract surgery. The aspiration line 1155 removes fluid and emulsified lens particles from the eye during cataract surgery.

When irrigation fluid exits irrigation fluid source 1105, it travels through irrigation line 1140 and into the eye 1145. An irrigation pressure sensor 1130 measures the pressure of the irrigation fluid in irrigation line 1140. An optional irrigation valve 1135 is also provided for on/off control of irrigation. Irrigation pressure sensor 1130 is implemented by any of a number of commercially available fluid pressure sensors and can be located anywhere in the irrigation fluid path (anywhere between the irrigation source 1105 and the eye 1145).

Figure 2:
FIG. 2 is a perspective view of an irrigation source with identification features according to the principles of the present invention.

A hand piece 1150 is placed in the eye 1145 during a phacoemulsification procedure. The hand piece 1150 has a hollow needle (as seen in FIG. 2) that is ultrasonically vibrated in the eye to break up the diseased lens. A sleeve located around the needle provides irrigation fluid from irrigation line 1140. The irrigation fluid passes through the space between the outside of the needle and the inside of the sleeve (as more clearly shown in FIG. 2A). Fluid and lens particles are aspirated through the hollow needle. In this manner, the interior passage of the hollow needle is fluidly coupled to aspiration line 1155. Pump 1170 draws the aspirated fluid from the eye 1145. An aspiration pressure sensor 1160 measures the pressure in the aspiration line. An optional vent valve can be used to vent the vacuum created by pump 1170. The aspirated fluid passes through reservoir 1175 and into drain bag 1180.

FIG. 2 is a perspective view of an irrigation source with identification features according to the principles of the present invention. In FIG. 2, an irrigation bag 200 has an outlet port 210. Bag 200 may be made of any flexible material, such as a polymer. Bag 200 may be configured to be hung from an IV pole or used with a squeezing mechanism that pressurizes the contents of bag 200. Port 210 provides an outlet for fluid in bag 200 and is described in more detail below.

Figure 3A:
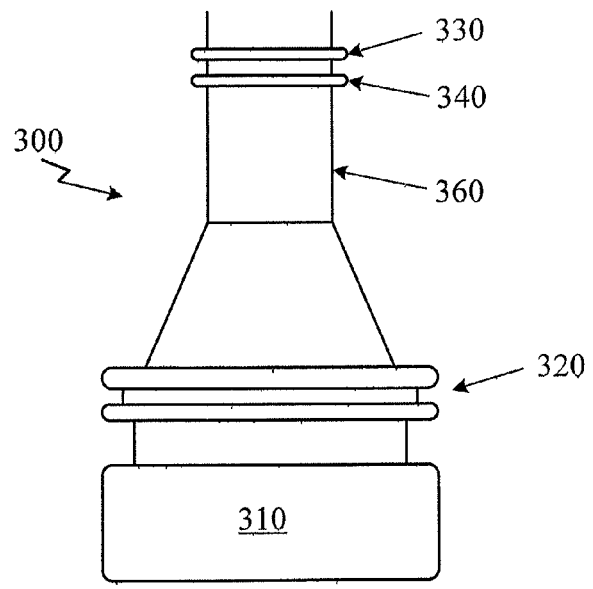
FIGS. 3A-3C are views of the port end of an irrigation fluid source according to the principles of the present invention.
Figures 3B, 3C:
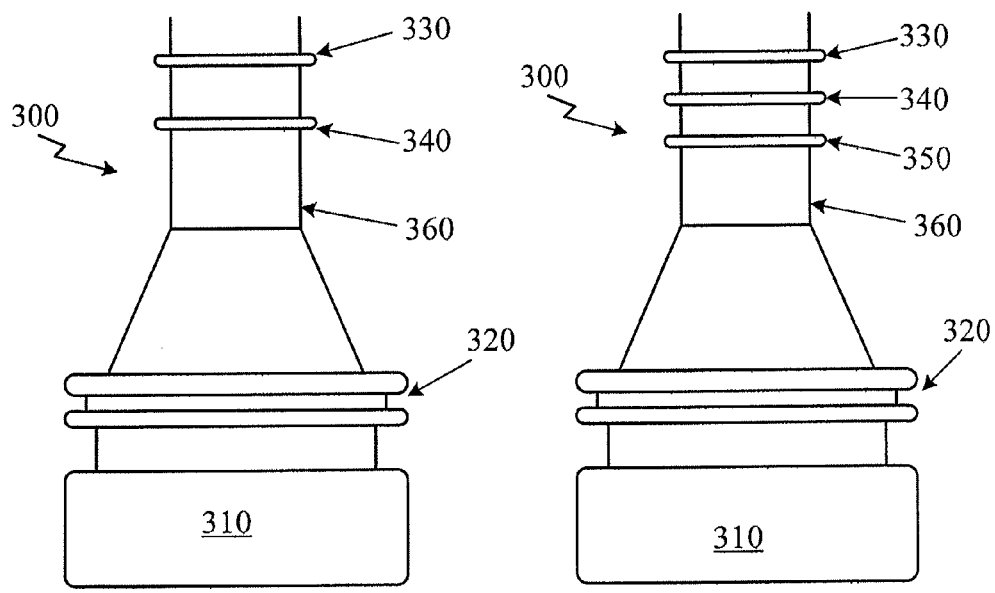

FIGS. 3A-3C are views of the port end of an irrigation fluid source according to the principles of the present invention. In FIG. 3A, port 300 includes spike port 310, alignment features 320, and protrusions 330 and 340 located on neck 360. Spike port 310 accepts an IV spike that fluidly connects tubing with the contents of the irrigation bag. As such, spike port seals the contents of the irrigation bag. Alignment features 320 serve to place the neck 360 in a specific location so that protrusions 330 and 340 can be imaged.

Protrusions 330 and 340 serve to identify the contents of the irrigation source. In one embodiment of the present invention, the distance or spacing between protrusions 330 and 340 can be detected to determine the contents of the irrigation source. For example, if the protrusions 330 and 340 are close together as shown in FIG. 3A, such close spacing can be used to determine the contents of the irrigation source. As shown in FIG. 3B, the distance or spacing between protrusions 330 and 340 is greater than that depicted in FIG. 3A. In this manner, the greater spacing shown in FIG. 3B can be used to indicate different contents in the irrigation source. In this manner, two protrusions 330 and 340 may be used with the distance or spacing between them indicating the contents of the irrigation source to which they are attached. For example, the distance between protrusions 330 and 340 may be one centimeter in FIG. 3A and three centimeters in FIG. 3B. Numerous other distances may be employed as well—such as providing protrusions 330 and 340 with distances that differ by a centimeter from a distance of one centimeter to a distance of ten centimeters. In this manner, ten different unique identifiers are provided. In another example, protrusions 330 and 340 is FIG. 3A are a distance of two centimeters apart, and protrusions 330 and 340 in FIG. 3B are a distance of six centimeters apart providing two unique identifiers. When using two protrusions, a distance between them can indicate the contents of the irrigation source to which they are attached.

In another embodiment of the present invention, a number of protrusions 330, 340, and 350 may be used to determine the contents of the irrigation source as shown in FIG. 3C. In this manner, three protrusions 330, 340, and 350 provide an indication of the irrigation source contents to which the port is attached. The two protrusions shown in FIGS. 3A and 3B may each provide different identifiers based on the number of protrusions present. Any number of protrusions may be used to provide such an identifier. For example, from one to six protrusions may be used to provide six different identifiers. In addition, the absence of a protrusion may also be an identifier.

In other embodiments of the present invention, the shape of the protrusion, the distance a protrusion extends from the neck 360, the color of the protrusion, or other visual difference may be used to provide unique identifiers. In this manner, a single visual difference or a combination of visual differences may be used. In FIGS. 3A-3C, the protrusions 330 and 340 are circumferential ridges located around the periphery of the neck 360

Finally, any combination of the above visual differences may be employed to provide identifiers. For example, one may use the number of protrusions as well as the distance or spacing between protrusions to provide identifiers. In this manner, protrusions 330 and 340 in FIG. 3A are both closer together and different in number than protrusions 330, 340, and 350 in FIG. 3C. The combination of the number of protrusions and the distance between the protrusions can be used to provide a greater number of unique identifiers for irrigation sources. Regardless of the type of protrusions used, the unique identifier may be represented by a subset of a grouping of protrusions.

Figure 4:
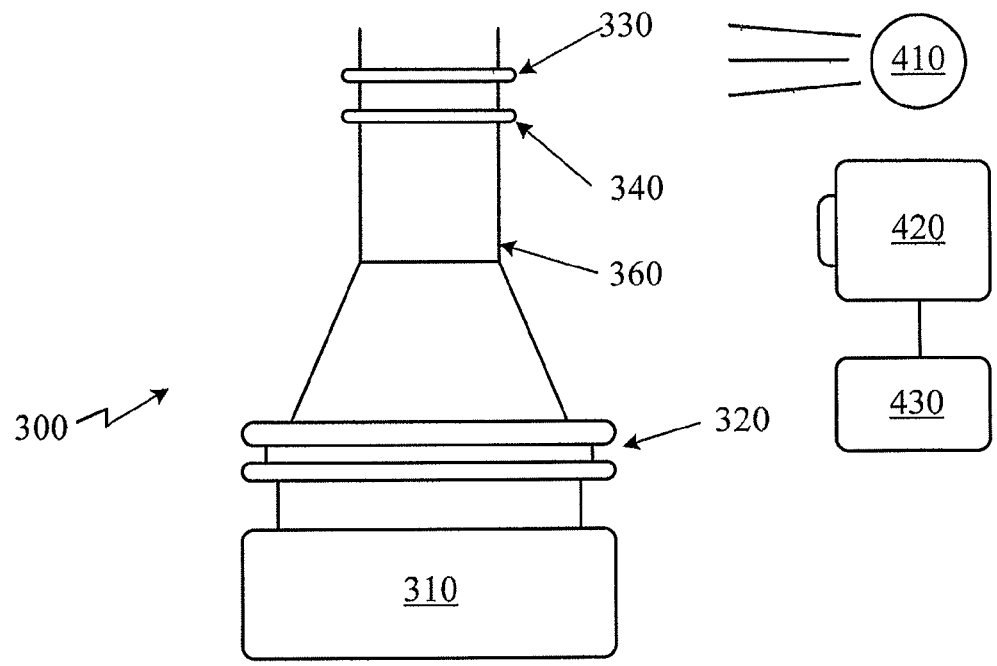
FIG. 4 is a diagram of an irrigation source identification system according to the principles of the present invention.

FIG. 4 is a diagram of an irrigation source identification system according to the principles of the present invention. In FIG. 4, port 300 is located adjacent to light source 410 and imaging device 420. Imaging device 420 is coupled to a processor 430. Imaging device 420 images the neck 360 and protrusions 330 and 340 to determine which identifier is presented. The identifier determines the contents of the irrigation source to which port 300 is attached. Light source 410 is most typically a light emitting diode or diode array, though other common light sources may be employed. In another embodiment of the present invention, ambient light or light present in the room may be used, in which case light source 410 is absent. In other embodiments of the present invention, light source 410 is located adjacent to imaging device 420, opposite imaging device 420, or adjacent to neck 360 so that it illuminates neck 360. Imaging device 420 is most typically a CMOS-type camera chip, though other small imaging devices may be employed. For example, imaging device may be a CCD-type chip or other semiconductor or wafer mounted device. Processor 430 may be any of a number of different microprocessors, microcontroller, ASIC, or special purpose semiconductors.

Figure 5:
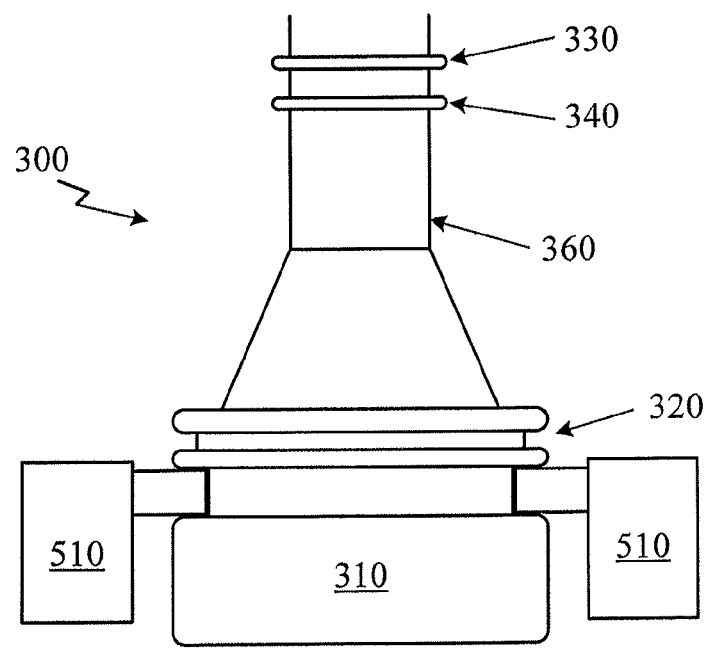
FIG. 5 is a diagram of an alignment and clamping mechanism for use with an irrigation source identification system according to the principles of the present invention.

FIG. 5 is a diagram of an alignment and clamping mechanism for use with an irrigation source identification system according to the principles of the present invention. In FIG. 5, clamping device 510 holds port 300 in place in a surgical console. Clamping device 510 also serves to properly align neck 360 so that it can be imaged (and optionally illuminated). Clamping device 510 is most typically motorized so that it automatically grabs port 300 between alignment features 310 and spike port 310. Since each irrigation source has the same alignment features 320 and spike port 310, consistent placement of the irrigation source and alignment of neck 360 is achieved. In other embodiments, clamping device can be manual or have manual aspects. For example, a groove on clamping device 510 may align with the alignment features 320 and spike port 310 of port 300. In one embodiment of the present invention, clamping device 510 is located in a phacoemulsification console (not shown). Port 300 of the irrigation source may be placed in a collar located in the console. Clamping device 510 may then hold the port 300 (and attached irrigation source) in place.

In operation, port 300 is placed into a clamping device that both holds port 300 and aligns neck 360. The neck 360 of the irrigation source is aligned so that the imaging device 420 can image it. The neck 360 is optionally illuminated. Imaging device 420 images the neck 360 and protrusions 330 and 340. The image taken by imaging device 420 is compared with images stored in memory to determine which identifier the protrusions 330 and 340 represent. Such comparison may be made on the basis of contrast, color, sharpness, or other image attribute and may be made by processor 430.

From the above, it may be appreciated that the present invention provides an improved system for identifying an irrigation source. The present invention provides an irrigation source with a port features that can be identified by an imaging system. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An irrigation source comprising:
a container for holding a quantity of irrigation fluid;
a port fluidly coupled to and integral with the container, the port having an outlet end and a neck, the neck having a plurality of identifying protrusions selected from a grouping of protrusions, the plurality of identifying protrusions providing a unique identifier for the container; and
an alignment feature disposed on the neck, the alignment feature comprising two circumferential protrusions arranged to form an annular gap between the two protrusions, the annular gap arranged to receive a clamping device so that the plurality of identifying protrusions is aligned with an imaging device.

2. The irrigation source of claim 1 wherein the unique identifier is based on a distance between at least two of the plurality of identifying protrusions.

3. The irrigation source of claim 1 wherein the unique identifier is based on a number of the identifying protrusions.

4. The irrigation source of claim 1 wherein the unique identifier is based on a shape of the plurality of identifying protrusions.

5. The irrigation source of claim 1 wherein the unique identifier is based on a color of the plurality of identifying protrusions.

6. The irrigation source of claim 1 wherein the plurality of identifying protrusions is each a circumferential ridge located around the periphery of the neck.

7. An irrigation source identification system comprising:
an irrigation source comprising a container for holding a quantity of irrigation fluid and a port fluidly coupled to and integral with the container, the port having an outlet end and a neck, the neck having a plurality of identifying protrusions selected from a grouping of protrusions, the plurality of identifying protrusions providing a unique identifier for the container;
an alignment feature disposed on the neck, the alignment feature comprising two circumferential protrusions arranged to form an annular gap between the two protrusions, the annular gap arranged to receive a clamping device so that the plurality of identifying protrusions is aligned with an imaging device;
an imaging device located adjacent to the neck of the irrigation source; and
a processor coupled to the imaging device;
wherein the imaging device images the neck and the plurality of identifying protrusions of the irrigation source and the processor determines which identifier is associated with the image.

8. The irrigation source identification system of claim 7 further comprising:
a light source located near the neck.

9. The irrigation source identification system of claim 7 further comprising:
a clamping device for holding the port and aligning the neck with the imaging device.

10. The irrigation source identification system of claim 7 wherein the processor determines which identifier is associated with the image based on a distance between at least two of the plurality of identifying protrusions.

11. The irrigation source identification system of claim 7 wherein the processor determines which identifier is associated with the image based on a number of the identifying protrusions.

12. The irrigation source identification system of claim 7 wherein the processor determines which identifier is associated with the image based on a shape of the plurality of identifying protrusions.

13. The irrigation source identification system of claim 7 wherein the processor determines which identifier is associated with the image based on a color of the plurality of identifying protrusions.

14. The irrigation source identification system of claim 7 wherein the plurality of identifying protrusions is each a circumferential ridge located around the periphery of the neck.

15. An irrigation source comprising:
a container for holding a quantity of irrigation fluid;
a port fluidly coupled to and integral with the container, the port having an outlet end and a generally cylindrical neck, the generally cylindrical neck having a plurality of circumferential protrusions selected from a grouping of circumferential protrusions, the plurality of circumferential protrusions extending from the neck around a periphery of the neck, the plurality of circumferential protrusions providing a unique identifier for the container and an alignment feature disposed on the neck, the alignment feature comprising a plurality of protrusions arranged to form an annular gap between at least two of the protrusions, the annular gap arranged to receive a clamping device so that the plurality of circumferential protrusions is aligned with an imaging device.

16. The irrigation source of claim 15 wherein in a group of irrigation sources, the alignment feature of each of the group of irrigation sources is the same and the plurality of circumferential protrusions on each of the group of irrigation sources is different.

* * * * *